(12) United States Patent
Barnes et al.

(10) Patent No.: US 9,221,750 B2
(45) Date of Patent: Dec. 29, 2015

(54) PROCESS FOR PREPARING AN INTERNAL OLEFIN SULFONATE

(71) Applicant: SHELL OIL COMPANY, Houston, TX (US)

(72) Inventors: Julian Richard Barnes, Amsterdam (NL); Hendrik Dirkzwager, Amsterdam (NL); Robert Moene, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/383,134

(22) PCT Filed: Feb. 22, 2013

(86) PCT No.: PCT/EP2013/053618
§ 371 (c)(1),
(2) Date: Sep. 5, 2014

(87) PCT Pub. No.: WO2013/131766
PCT Pub. Date: Sep. 12, 2013

(65) Prior Publication Data
US 2015/0073168 A1    Mar. 12, 2015

(30) Foreign Application Priority Data

Mar. 8, 2012 (EP) .................................. 12158649

(51) Int. Cl.
| | | |
|---|---|---|
| C07C 303/14 | (2006.01) | |
| C07C 305/02 | (2006.01) | |
| C07C 303/06 | (2006.01) | |
| C07C 303/32 | (2006.01) | |
| C09K 8/584 | (2006.01) | |

(52) U.S. Cl.
CPC ............ *C07C 303/14* (2013.01); *C07C 303/06* (2013.01); *C07C 303/32* (2013.01); *C07C 305/02* (2013.01); *C09K 8/584* (2013.01)

(58) Field of Classification Search
USPC .................................................. 558/55, 44
See application file for complete search history.

(56) References Cited

U.S. PATENT DOCUMENTS

| | | |
|---|---|---|
| 4,183,867 A | 1/1980 | Sekiguchi et al. |
| 4,248,793 A | 2/1981 | Sekiguchi et al. |
| 5,510,306 A | 4/1996 | Murray |
| 5,633,422 A | 5/1997 | Murray |
| 5,648,584 A | 7/1997 | Murray |
| 5,648,585 A | 7/1997 | Murray et al. |
| 5,849,960 A | 12/1998 | Singleton et al. |

FOREIGN PATENT DOCUMENTS

| | | |
|---|---|---|
| EP | 0351928 | 1/1990 |
| WO | 9506632 | 3/1995 |
| WO | 9640587 | 12/1996 |
| WO | 0064867 | 11/2000 |
| WO | 2010129051 | 11/2010 |

OTHER PUBLICATIONS

Adami; "The Production of a-olefin Sulfonate by SO2 Sulfonation"; Handbook of Detergents, Part F: Production; Section 5.3.1; pp. 102-109; CRC Press; 2009.
Van Os, et al.; "Anionic Surfactants: Organic Chemistry"; Surfactant Science Series 56 Ed.; Chapter 7: Olefin Sulfonates; pp. 367-371; 1996.
Column, D.C.; "Two-phase Titration of Ionic Surfactants with Surfactants of Opposite Charge"; Introduction to Surfactant analysis—Basic Techniques; p. 59-64; 1994.
Colloid, J.; "Interfacial tensions and solubilizing ability of a microemulsion phase that coexists with oil and brine"; Journal of Colloid and Interface Science; vol. 71, No. 2; p. 408-426; 1979.

*Primary Examiner* — Kristin Vajda

(57) ABSTRACT

The invention relates to a process for preparing an internal olefin sulfonate, comprising sulfonating an internal olefin, having an average carbon number that is equal to or greater than 20, in a sulfonation reactor into sulfonated internal olefin followed by contacting sulfonated internal olefin with a base containing solution, wherein the sulfonation reactor is cooled with a cooling means having a temperature which is greater than 35° C. Further, the invention relates to an internal olefin sulfonate obtainable by said process, and to use of internal olefin sulfonates obtainable or obtained by said process as a surfactant, suitably as a surfactant in chemical Enhanced Oil Recovery.

13 Claims, 2 Drawing Sheets

PROCESS FOR PREPARING AN INTERNAL OLEFIN SULFONATE

PRIORITY CLAIM

The present application is the National Stage (§371) of International Application No. PCT/EP2013/053618, filed Feb. 22, 2013, which claims priority from European application no. 12158649.9, filed Mar. 8, 2012, the disclosures of which are incorporated herein by reference.

FIELD OF THE INVENTION

The present invention relates to a process for preparing an internal olefin sulfonate, and to an internal olefin sulfonate obtainable by said process.

BACKGROUND OF THE INVENTION

It is known to use internal olefin sulfonates (IOS) as a surfactant for a variety of applications including chemical Enhanced Oil Recovery (cEOR).

Further, it is known to prepare olefin sulfonates from alpha-olefins and internal olefins, by sulfonating the olefins, for example by contacting with sulfur trioxide as the sulfonating agent. This is followed by neutralizing and hydrolyzing the sulfonated olefin containing intermediate mixture which comprises alkene sulfonic acids and sultones that are to be converted into the desired sulfonates. Said neutralization step and subsequent hydrolysis step both comprise contacting sulfonated olefin with a base containing solution, for example an aqueous NaOH containing solution. The hydrolysis step is generally carried out at a higher temperature than the temperature in the neutralization step, and is aimed at completing the reaction of the base with sulfonated olefin. See for example Adami, "The Production of α-Olefin Sulfonate by $SO_3$ Sulfonation", Section 5.3.1, pages 102-109, Handbook of Detergents, Part F: Production, CRC Press, 2009.

Further, EP0351928A1 discloses a process for the preparation of internal olefin sulfonates which comprises reacting in a film reactor an internal olefin having from 8 to 26 carbon atoms with a sulfonating agent, in a mol ratio of sulfonating agent to internal olefin of 1:1 to 1.25:1 while cooling the reactor with a cooling means having a temperature not exceeding 35° C., and allowing to neutralize and hydrolyze the reaction product from the sulfonation step.

More in particular, in Examples 1-7 of EP0351928A1, a sulfonation process was carried out wherein a mixture of $C_{13-14}$ internal olefins was contacted with sulfur trioxide in a stainless steel reactor tube. The reactor tube was cooled by flowing water of low temperature along the outside of the reactor tube in a direction opposite to the direction of the feed/$SO_3$ stream through the reactor tube. In Examples 1-4, the cooling water had an inlet temperature of 8° C. and an outlet temperature of 13° C. In Example 5, the cooling water had an inlet temperature of 10° C. and an outlet temperature of 15° C., while in Examples 6 and 7 the inlet temperature was 12° C. and the outlet temperature 17° C. That is to say, the above cooling water inlet temperatures are relatively far below the maximum of 35° C. taught in EP0351928A1. Indeed, EP0351928A1 discloses a preference for the cooling means temperature of only 0° C. to 25° C. Further, it is described that depending upon the circumstances even lower temperatures may be used. That is to say, the use of higher temperatures is not suggested at all in EP0351928A1.

It is an object of the present invention to provide a process for preparing an internal olefin sulfonate which process is suitable for preparing the sulfonates from internal olefins having an average carbon number that is equal to or greater than 20. A further object of the present invention is to provide internal olefin sulfonates, made from such internal olefins having an average carbon number that is equal to or greater than 20, that are suitable to be used as a surfactant in chemical Enhanced Oil Recovery (cEOR).

SUMMARY OF THE INVENTION

Surprisingly it was found that internal olefin sulfonates can suitably be prepared from internal olefins having an average carbon number that is equal to or greater than 20, by a sulfonation process wherein the sulfonation reactor is cooled with a cooling means having a temperature which is greater than 35° C. In addition, it was found that the internal olefin sulfonates thus prepared have properties which make them suitable to be used as a surfactant in chemical Enhanced Oil Recovery (cEOR).

Accordingly, the present invention relates to a process for preparing an internal olefin sulfonate, comprising sulfonating an internal olefin, having an average carbon number that is equal to or greater than 20, in a sulfonation reactor into sulfonated internal olefin followed by contacting sulfonated internal olefin with a base containing solution, wherein the sulfonation reactor is cooled with a cooling means having a temperature which is greater than 35° C.

Further, the present invention relates to an internal olefin sulfonate obtainable by said process.

Still further, the present invention relates to use of internal olefin sulfonates obtainable or obtained by said process as a surfactant, suitably as a surfactant in chemical Enhanced Oil Recovery.

DETAILED DESCRIPTION OF THE INVENTION

Figure 1A:
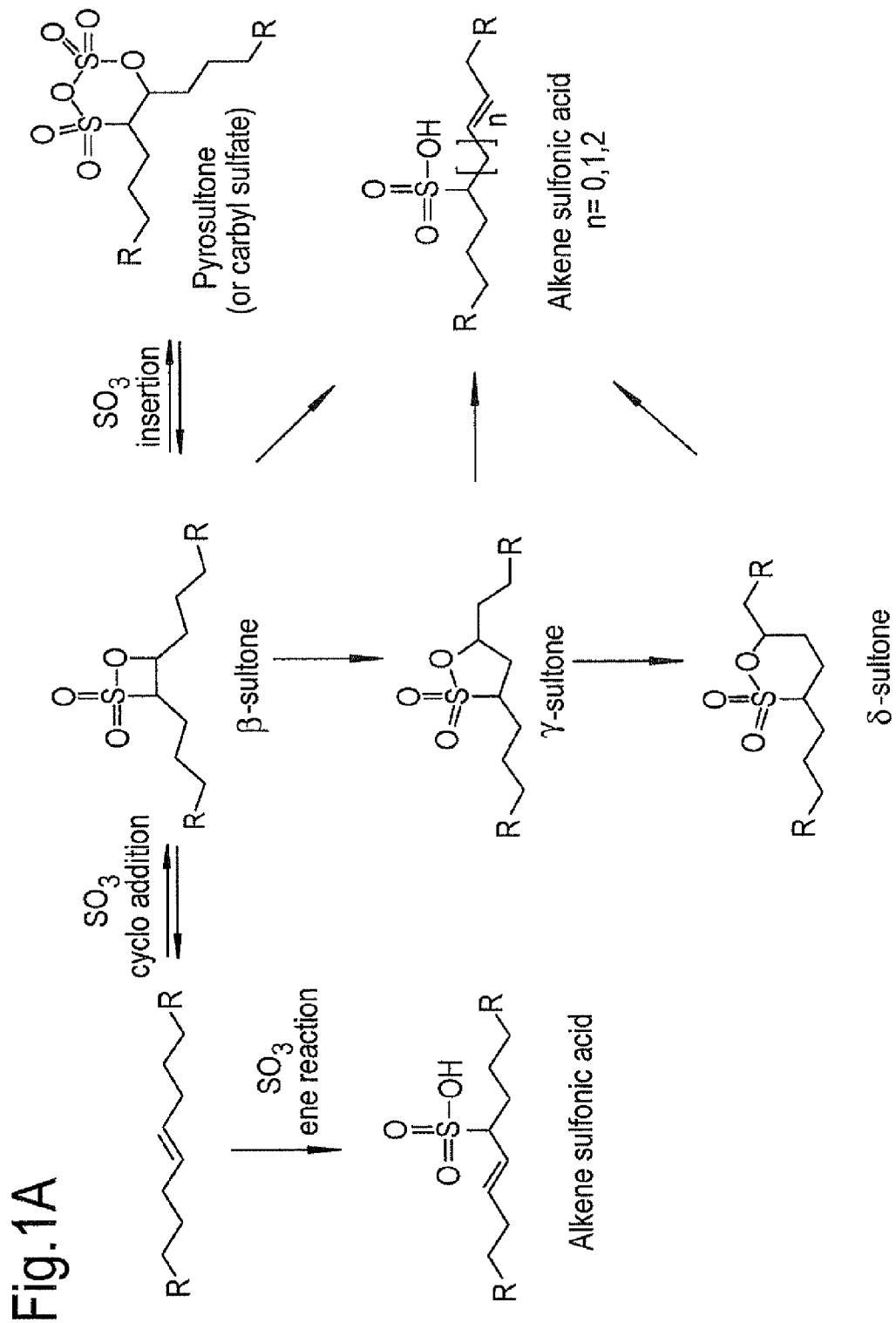
FIG. 1A illustrates the chemical reactions of an internal olefin with sulfur trioxide (sulfonating agent) during a sulfonation process.

The process of the present invention is a process for preparing an internal olefin sulfonate (IOS) from an internal olefin. Within the present specification, an internal olefin and an IOS comprise a mixture of internal olefin molecules and a mixture of IOS molecules, respectively. That is to say, within the present specification, "internal olefin" as such refers to a mixture of internal olefin molecules whereas "internal olefin molecule" refers to one of the components from such internal olefin. Analogously, within the present specification, "IOS" or "internal olefin sulfonate" as such refers to a mixture of IOS molecules whereas "IOS molecule" or "internal olefin sulfonate molecule" refers to one of the components from such IOS.

Branched IOS molecules are IOS molecules derived from internal olefin molecules which comprise one or more branches. Linear IOS molecules are IOS molecules derived from internal olefin molecules which are linear, that is to say which comprise no branches (unbranched internal olefin molecules). An internal olefin may be a mixture of linear internal olefin molecules and branched internal olefin molecules. Analogously, an IOS may be a mixture of linear IOS molecules and branched IOS molecules.

Within the present specification, an internal olefin or IOS may be characterised by its carbon number, branched content and/or molecular weight. In case reference is made to an average carbon number and/or average molecular weight, this means that the internal olefin or IOS in question is a mixture of molecules which differ from each other in terms of carbon number and/or molecular weight.

Within the present specification, said average carbon number is determined by multiplying the number of carbon atoms of each internal olefin molecule or IOS molecule by the weight fraction of that molecule and then adding the products, resulting in a weight average carbon number. The average carbon number may be determined by GC analysis.

Within the present specification, branched content is determined by dividing the amount of branched molecules by the total amount of branched and unbranched molecules. The branched content may be determined by GC analysis.

Within the present specification, said average molecular weight is determined by multiplying the molecular weight of each internal olefin molecule or IOS molecule by the mole fraction or weight fraction of that molecule and then adding the products, resulting in a number average or weight average molecular weight, respectively. The molecular weight may be determined by GC analysis In the present invention, an internal olefin sulfonate is prepared from an internal olefin in a process comprising at least 2 consecutive steps: sulfonation followed by reaction with a base.

In the sulfonation step of the present process, an internal olefin is sulfonated. In the present invention, the internal olefin has an average carbon number that is equal to or greater than 20. That is to say, the average carbon number is at least 20, preferably at least 21, more preferably at least 22, more preferably at least 23, more preferably at least 24, most preferably at least 25. Further, preferably, the average carbon number is at most 40, preferably at most 35, more preferably at most 32, more preferably at most 30, most preferably at most 28. The average carbon number may be of from 20 to 40, suitably 21 to 35, more suitably 22 to 30, most suitably 23 to 28.

Further, in the sulfonation step of the present process, the sulfonation reactor is cooled with a cooling means having a temperature (before heat-exchange with the sulfonation reactor) which is greater than 35° C.

Preferably, the above-mentioned cooling means temperature is at least 36° C., more preferably at least 38° C., more preferably at least 40° C., more preferably at least 42° C., most preferably at least 43° C. Further, preferably, said cooling means temperature is at most 70° C., more preferably at most 65° C., more preferably at most 60° C., more preferably at most 57° C., more preferably at most 55° C., most preferably at most 53° C. Said cooling means temperature may be of from 40 to 60° C., suitably 42 to 53° C.

One particular suitable cooling means for cooling the reactor in the sulfonation step is a cooling fluid such as cooling water. As disclosed in EP0351928A1, also in the present invention, such cooling fluid may flow along the outside of the sulfonation reactor thereby effecting heat-exchange with the contents of that reactor, preferably in a direction opposite to the direction of the stream through the reactor.

Further, in the present invention, the branched content of the internal olefin used in the sulfonation step may be of from 0.1 to 30 wt. %, preferably 1 to 25 wt. %. Branches in the above-mentioned internal olefin molecules may include methyl, ethyl and/or higher molecular weight branches including propyl branches.

In the present invention, the number average molecular weight for the internal olefin may vary within wide ranges, such as from 200 to 600, suitably 250 to 500, more suitably 300 to 400 g/mole.

An IOS molecule is made from an internal olefin molecule whose double bond is located anywhere along the carbon chain. Internal olefin molecules may be made by double bond isomerization of alpha-olefin molecules whose double bond is located at a terminal position. Generally, such isomerization results in a mixture of internal olefin molecules whose double bonds are located at different internal positions. The distribution of the double bond positions is mostly thermodynamically determined. Further, that mixture may also comprise a minor amount of non-isomerized alpha-olefins. Still further, because the starting alpha-olefin may comprise a minor amount of paraffins (non-olefinic alkanes), the mixture resulting from alpha-olefin isomeration may likewise comprise that minor amount of unreacted paraffins.

In the present invention, the amount of alpha-olefins in the internal olefin may be up to 5%, for example 1 to 4 wt. % based on total composition. Further, in the present invention, the amount of paraffins in the internal olefin may be up to 15 wt. %, for example up to 12 wt. % based on total composition.

Suitable processes for making an internal olefin include those described in U.S. Pat. No. 5,510,306, U.S. Pat. No. 5,633,422, U.S. Pat. No. 5,648,584, U.S. Pat. No. 5,648,585, U.S. Pat. No. 5,849,960, EP0830315B1 and "Anionic Surfactants: Organic Chemistry", Surfactant Science Series, volume 56, Chapter 7, Marcel Dekker, Inc., New York, 1996, ed. H. W. Stacke.

In the sulfonation step of the present process, the internal olefin is contacted with a sulfonating agent. Referring to FIG. 1A, reaction of the sulfonating agent with an internal olefin leads to the formation of cyclic intermediates known as beta-sultones, which can undergo isomerization to unsaturated sulfonic acids and the more stable gamma- and delta-sultones.

In the present invention, the sulfonating agent may be sulfur trioxide ($SO_3$), sulfuric acid or oleum, of which sulfur trioxide is preferred. Further, in the present invention, the mole ratio of sulfonating agent to internal olefin may be 0.5:1 to 2:1, more suitably 0.8:1 to 1.8:1, most suitably 1:1 to 1.6:1.

In case sulfur trioxide is the sulfonating agent in the present process, the sulfur trioxide is preferably provided as a gas stream comprising a carrier gas and the sulfur trioxide. The carrier gas may be air or an inert gas, such as nitrogen. The concentration of sulfur trioxide in said gas stream may be 1 to 10 vol. %, more suitably 2 to 8 vol. %, most suitably 2 to 7 vol. %, based on the volume of the carrier gas.

The sulfonation reaction with $SO_3$ is preferably carried out in a film reactor, for example a "falling-film reactor", where the olefin feed is continuously fed onto the inside surfaces of a tube and gaseous $SO_3$ is fed into the tube to react with the (falling) olefin film in a controlled manner. The reactor is cooled with a cooling means, which is preferably water, for example by flowing the cooling means at the outside walls of the reactor, as discussed above. In the present invention, the sulfonation reactor is cooled with a cooling means having a temperature which is greater than 35° C.

The sulfonating agent may be added separately from or in combination with the internal olefin to the sulfonation reactor. It is preferred that in the present invention, just like said cooling means temperature for the sulfonation reactor, also the feedstream or feedstreams to the sulfonation reactor comprising the sulfonating agent and the internal olefin have a temperature which is greater than 35° C. The above-mentioned preferences for said cooling means temperature also apply to these feedstream temperatures.

The present process may be carried out batchwise, semi-continuously or continuously, preferably continuously. In particular, the sulfonation step may be carried out batchwise, semi-continuously or continuously. Preferably, the sulfonation step is carried out continuously.

In the present invention, after sulfonating the internal olefin into sulfonated internal olefin, the latter is contacted with a base containing solution. Within the present specification, "base containing solution" implies that the base is dissolved in a solvent, thereby forming said solution, when the base is contacted with sulfonated internal olefin. Said solvent is thus a solvent for the base, which solvent is preferably water.

Preferably, sulfonated internal olefin from the sulfonation step of the present process is directly, without removing any molecules, subjected to the reaction with the base. However, between the sulfonation step and the step wherein contacting with a base containing solution is performed in accordance with the present invention, there may still be an intermediate step. Such intermediate step may for example be a step what is generally referred to as "aging", which is commercially applied in the manufacture of alpha-olefin sulfonates. Such aging step may be performed in a way as described by Van Os et al. in "Anionic Surfactants: Organic Chemistry", Surfactant Science Series 56, ed. Stacke H. W., 1996, Chapter 7: Olefin sulfonates, pages 368-369, the disclosure of which is incorporated herein by reference.

Figure 1B:
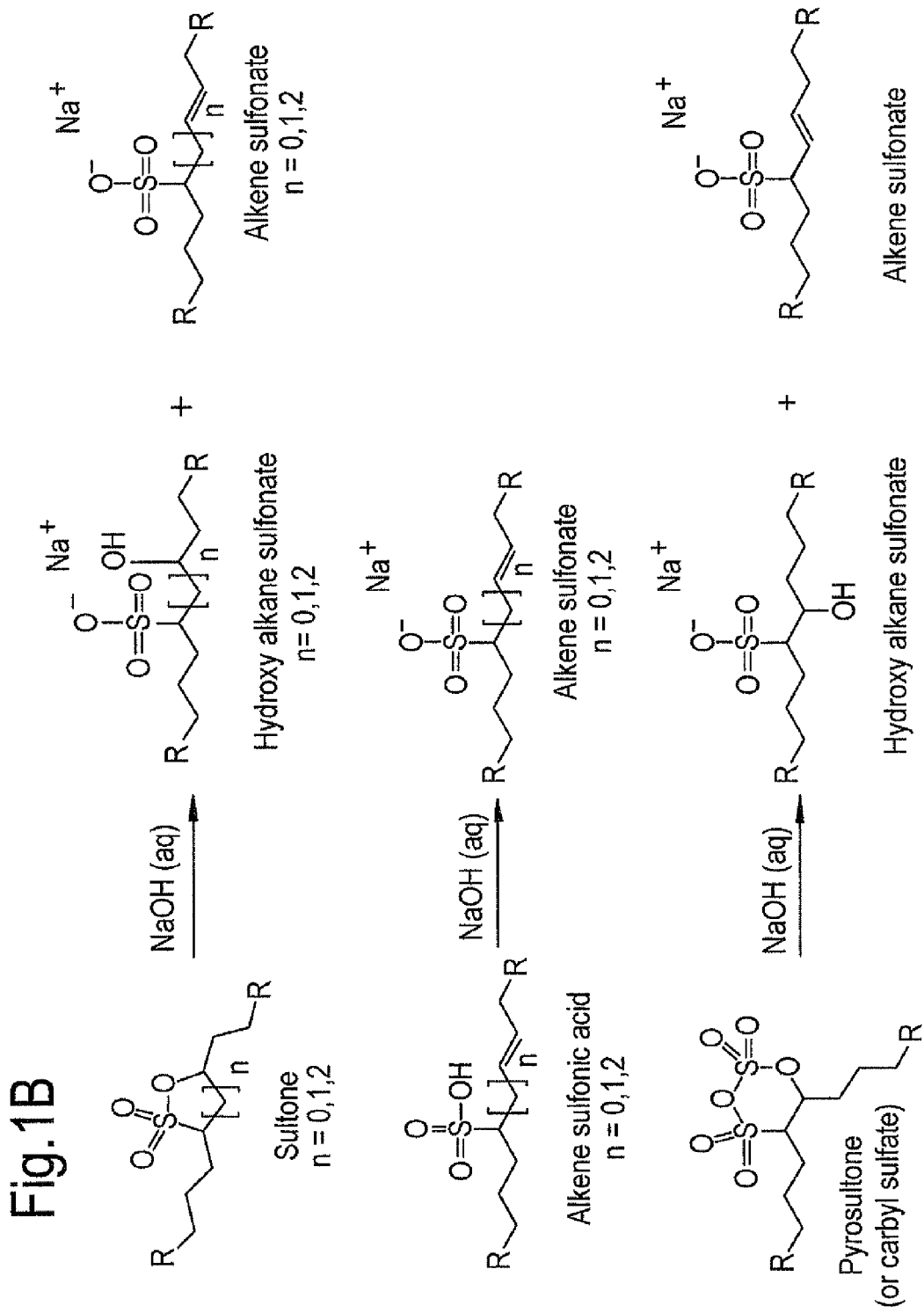
FIG. 1B illustrates the subsequent chemical reactions of a neutralization and hydrolysis process to form an internal olefin sulfonate.

In the next step of the present process, sulfonated internal olefin from the sulfonation step is contacted with a base containing solution. Referring to FIG. 1B, in this step, beta-sultones are converted into beta-hydroxyalkane sulfonates, whereas gamma- and delta-sultones are converted into gamma-hydroxyalkane sulfonates and delta-hydroxyalkane sulfonates, respectively. Part of said hydroxyalkane sulfonates may be dehydrated into alkene sulfonates.

Thus, referring to FIGS. 1A and 1B, an IOS comprises a range of different molecules, which may differ from one another in terms of carbon number, being branched or unbranched, number of branches, molecular weight and number and distribution of functional groups such as sulfonate and hydroxyl groups. An IOS comprises both hydroxyalkane sulfonate molecules and alkene sulfonate molecules and possibly also di-sulfonate molecules. Hydroxyalkane sulfonate molecules and alkene sulfonate molecules are shown in FIG. 1B. Di-sulfonate molecules (not shown in FIG. 1B) originate from a further sulfonation of for example an alkene sulfonic acid as shown in FIG. 1A.

The base to be contacted with sulfonated internal olefin from the sulfonation step may be a water soluble base, which is preferably selected from the group consisting of hydroxides, carbonates and bicarbonates of an alkali metal ion, such as sodium or potassium, or of ammonium ion, and amine compounds. Suitable examples are sodium hydroxide and sodium carbonate, most suitably sodium hydroxide. Further, preferably, the solvent for the base is water. Preferably, in this step, sulfonated internal olefin is contacted with an aqueous solution of a water soluble base, such as described hereinabove, especially sodium hydroxide.

The reaction in this step is generally carried out with an excessive molar amount of base. It is preferred that the final internal olefin sulfonate product is not acidic because this may lead to corrosion of process equipment and/or to disintegration of the internal olefin sulfonate. Therefore, it is preferred that the final internal olefin sulfonate product contains a certain amount of base, for example 0.1 to 2 wt. % based on 100% of the active matter. This may be achieved by choosing the amount of base to be added such that the molar ratio of (i) the amount of base fed to the step wherein sulfonated internal olefin is contacted with the base containing solution to (ii) the amount of sulfonating agent (e.g. $SO_3$) fed to the sulfonation step is higher than 1, suitably higher than 1 up to 1.4, more suitably 1.1 to 1.3.

The base and the solvent for the base may be added separately. Preferably, the base is added as part of a solution as described above. Additional solvent may be added separately in addition to such base containing solution. If the base is added as part of a solution, the concentration of the base in such solution, based on total solution, is suitably at most 60 wt. %, more suitably 10 to 55 wt. %, most suitably 20 to 55 wt. %.

The temperature at which sulfonated internal olefin is contacted with the base containing solution in the present process may vary within wide ranges, for example 0 to 250° C. Further, the time for the reaction between the base and sulfonated internal olefin may also vary within wide ranges, for example 5 minutes to 4 hours.

In the step wherein sulfonated internal olefin is contacted with the base containing solution, a non-ionic surfactant may also be added as a process aid. Such non-ionic surfactant may help in increasing the mobility of the reaction mixture such that the reaction mixture can be handled well enough (e.g. in terms of storage, pumping, mass transfer). Preferably, the non-ionic surfactant is an alkoxylate of an alcohol having an aliphatic group, preferably an ethoxylate of such alcohol. Said alcohol may be primary or secondary, preferably primary. Said alcohol alkoxylate may be of the following formula:

$$R\text{—}O\text{—}[R'\text{—}O]_x\text{—}H \quad (I)$$

wherein R is the aliphatic group originating from the alcohol, R'—O is an alkylene oxide group, and x represents the number of such alkylene oxide groups.

The non-ionic surfactant of above exemplary formula (I) comprises a range of different molecules which may differ from one another in terms of carbon number for the aliphatic group R, the aliphatic group R being branched or unbranched (linear), nature and number of alkylene oxide groups R'—O, and molecular weight. Thus, the non-ionic surfactant of above exemplary formula (I) comprises a mixture of non-ionic surfactant molecules. That is to say, within the present specification, "non-ionic surfactant" as such refers to a mixture of non-ionic surfactant molecules whereas "non-ionic surfactant molecule" refers to one of the components from such non-ionic surfactant.

The weight average carbon number for the aliphatic group R from the optional non-ionic surfactant of above exemplary formula (I) is not essential and may vary within wide ranges, such as from 4 to 25, suitably 6 to 20, more suitably 8 to 15. Further, preferably, said aliphatic group is linear.

The alkylene oxide groups R'—O in above exemplary formula (I) may comprise any alkylene oxide groups. For example, said alkylene oxide groups may comprise ethylene oxide groups, propylene oxide groups and butylene oxide groups or a mixture thereof, such as a mixture of ethylene oxide and propylene oxide groups. In case of a mixture of ethylene oxide and propylene oxide groups, the mixture may be random or blockwise. Preferably, said alkylene oxide groups consist of ethylene oxide groups.

In above exemplary formula (I), x represents the number of alkylene oxide groups R'—O. In the present invention, for the optional non-ionic surfactant of above exemplary formula (I), the average value for x is at least 0.5. Said average value for x may be of from 1 to 20, more suitably 4 to 16, most suitably 7 to 13.

Further, the number average molecular weight for the optional non-ionic surfactant of above exemplary formula (I) may be 300 to 700 g/mole, more suitably 400 to 600 g/mole, most suitably 450 to 550 g/mole.

As mentioned above, such non-ionic surfactant may increase mobility, thereby improving intimate mixing of the product from the sulfonation step with the base containing solution. In such way, contact between the organic phase and the base containing aqueous phase is improved. This improves mass transfer and promotes the desired reaction of the sultones and alkene sulfonic acids with the base, and avoids as much as possible the reverse reaction of beta-sultones into internal olefins and $SO_3$. Alternatively or additionally, this may be achieved by efficient stirring or by the addition of a co-solvent (such as a lower alcohol).

The step wherein sulfonated internal olefin is contacted with the base containing solution may be carried out batchwise, semi-continuously or continuously. Preferably, said step is carried out continuously. Further, a continuously stirred tank reactor (CSTR) and/or a plug flow reactor may be used in this step. Suitable reactors for this step comprise a loop reactor and a wiped film evaporator (WFE).

The step of the present process wherein sulfonated internal olefin is contacted with a base containing solution may be carried out as 2 separate, consecutive steps: a "neutralization step" followed by a "hydrolysis" step. In the present specification, "neutralization step" means the step wherein sulfonated internal olefin from the sulfonation step is contacted with a base containing solution for the first time. Further, in the present specification, "hydrolysis step" means the step that may follow after the former "neutralization step". The above features equally apply to said neutralization step and hydrolysis step separately.

In the present invention, the neutralization step may be carried out batchwise or continuously. Preferably, the neutralization step is carried out continuously. Suitable reactors for the neutralization step comprise a loop reactor and a wiped film evaporator (WFE). The hydrolysis step may also be carried out batchwise or continuously. Preferably, the hydrolysis step is carried out continuously. Preferably, a plug flow reactor is used in the hydrolysis step.

The neutralization step is preferably carried out at a temperature in the range of from 0 to 90° C., more preferably 10 to 80° C., more preferably 20 to 70° C., most preferably 30 to 60° C. The neutralization time may be 5 minutes to 4 hours.

Preferably, the product from the neutralization step is directly, without extracting unreacted internal olefin molecules and without removing the base and solvent, subjected to hydrolysis.

In the hydrolysis step, the product from the neutralization step is further reacted to complete conversion into sulfonate compounds. Said hydrolysis step is therefore preferably carried out at an elevated temperature, for example in order to convert sultones, especially delta-sultones, into active matter. Preferably, the temperature in the hydrolysis step is higher than the temperature in the neutralization step. Preferably, the temperature in the hydrolysis step is higher than 90 to 250° C., more preferably 95 to 220° C., more preferably 100 to 190° C., most preferably 140 to 180° C. The hydrolysis time may be 30 minutes to 4 hours.

U.S. Pat. No. 4,183,867, U.S. Pat. No. 4,248,793 and EP0351928A1, the disclosures of all of which are incorporated herein by reference, disclose processes which can be used to make internal olefin sulfonates in the process of the present invention. Further, the internal olefin sulfonates may be synthesized in a way as described by Van Os et al. in "Anionic Surfactants: Organic Chemistry", Surfactant Science Series 56, ed. Stacke H. W., 1996, Chapter 7: Olefin sulfonates, pages 367-371, the disclosure of which is incorporated herein by reference.

After reaction of sulfonated internal olefin with the base in accordance with the present invention, the internal olefin sulfonate (IOS) product may be diluted, for example by adding additional solvent (e.g. water), for example in case one wishes to facilitate the handling of that product in the application for which the IOS product is intended.

The invention is further illustrated by the following Examples.

EXAMPLES

General Experimental Set-Up

In the present Examples, sulfonation, neutralization and hydrolysis of the internal olefin feedstock in question were carried out in a continuous process.

Sulfonation was carried out in a falling-film reactor. The reactor length (L) was 6 metres and the reactor diameter (d) was 1 inch (2.54 cm). The sulfonating agent was $SO_3$ that was generated in situ by burning sulphur to $SO_2$ using dried air and converting the $SO_2$ from the air stream into $SO_3$ in a catalyst bed. Both said air stream, containing 5 vol. % of $SO_3$, and the internal olefin feedstock were then fed to the sulfonation reactor at an inlet temperature of 45 or 50° C. The molar ratio of $SO_3$ fed to the reactor to olefin fed to the reactor was varied by varying the amount of olefin fed. The $SO_3$ feedstream was maintained at a constant addition rate of approximately 6 kg/hour in all experiments. Said molar ratio was either 1.06 or 1.30. The reactor was cooled with cooling water which flowed along the outside of the reactor, thereby effecting heat-exchange with the contents of that reactor, in a direction opposite to the direction of the stream through the reactor. The cooling water had a temperature (before heat-exchange), that is to say an inlet temperature, of either 45 or 50° C.

Neutralization was carried out in a neutralization reactor which was either a loop reactor having a volume of 24 litres or a wiped film evaporator (WFE). Further parameters for the WFE used: diameter=0.207 metre, heat exchange area=0.75 $m^2$, 590 rpm/50 Hz, atmospheric pressure. The base used was NaOH, which was added to the neutralization reactor in the form of an aqueous NaOH solution. The NaOH concentration in said solution was either 30 wt. % or 50 wt. %, based on total amount of the solution. The amount of NaOH fed to the neutralization reactor was such that the molar ratio of NaOH fed to the neutralization reactor to $SO_3$ fed to the sulfonation reactor amounted to approximately 1.20. Either additional water was added, in addition to the water from said NaOH solution, or no additional water was added, depending on the desired active matter content. The temperature during neutralization was 50-55° C.

In addition, a non-ionic surfactant was added during neutralization in an amount of 5 wt. % (based on 100% of active matter). The non-ionic surfactant added was NEODOL™ 91-8 (hereinafter abbreviated as "N91-8"). N91-8 is an ethoxylate of NEODOL™ 91 which is a blend of mainly C9, C10 and C11 linear primary alcohols (C8 and lower=<1 wt. %; C9=18 wt. %; C10=42 wt. %; C11=38 wt. %; C12 and higher=1 wt. %; weight average carbon number=10.20). N91-8 comprises 8 ethoxylate units and has a number average molecular weight of about 513.

Hydrolysis was carried out in a non-stirred plug flow reactor, having a volume of 40 litres, to which the mixture from the neutralization reactor was fed directly. The temperature during hydrolysis was 170° C.

Properties of Internal Olefin Feed

Two types of internal olefin feedstocks were used, herein designated as "internal olefin I" and "internal olefin II". Both said feedstocks were mixtures comprising even and odd carbon number internal olefin molecules. In addition, the internal olefin feedstocks contained small amounts of paraffins and/or alpha-olefins. Properties of these feedstocks are shown in Table 1 below.

TABLE 1

| Composition in terms of carbon number (wt. %) | Internal olefin I | Internal olefin II |
|---|---|---|
| C14 | 0.00 | 0.10 |
| C15 | 0.60 | 0.90 |
| C16 | 0.80 | 1.10 |
| C17 | 1.00 | 1.50 |
| C18 | 1.70 | 2.50 |
| C19 | 3.40 | 4.80 |
| C20 | 5.20 | 7.10 |
| C21 | 6.20 | 8.20 |
| C22 | 6.90 | 8.40 |
| C23 | 7.10 | 8.00 |
| C24 | 7.30 | 8.20 |
| C25 | 7.20 | 6.70 |
| C26 | 7.60 | 6.10 |
| C27 | 6.50 | 5.90 |
| C28 | 6.40 | 5.10 |
| C29 | 5.70 | 4.60 |
| C30 | 5.20 | 4.20 |
| C31 | 4.60 | 3.60 |
| C32 | 4.20 | 3.20 |
| C33 | 3.10 | 2.40 |
| C34 | 2.40 | 1.90 |
| C35 | 1.90 | 1.40 |
| C36 | 1.40 | 1.20 |
| C37 | 1.00 | 0.80 |
| C38 | 0.70 | 0.60 |
| C39 | 0.50 | 0.40 |
| C40 | 0.40 | 0.30 |
| C41 | 0.30 | 0.20 |
| C42 | 0.20 | 0.20 |
| C43 | 0.20 | 0.10 |
| C44 | 0.20 | 0.20 |
| Weight average carbon number | 26.3 | 25.2 |
| Number average molecular weight (g/mole) | 354.05 | 339.10 |
| Alpha-olefins[1] (wt. %) | 1.3 | 1.2 |
| Paraffins[1] (wt. %) | 9.68 | 7.85 |
| Branched content[2] (wt. %) | 19.96 | 19.21 |

[1]Based on total composition.
[2]"Branched content" = amount of branched molecules based on total amount of branched and linear molecules.

Product Components in Samples

During the experiments, a sample of the mixture exiting the neutralization reactor prior to entering the hydrolysis reactor was taken, which was then analyzed. Further, a sample of the mixture exiting the hydrolysis reactor was taken, which was then also analyzed. The analyzed product properties were:

1. Active matter (AM) content (wt. % on 100% mixture): content of anionic internal olefin sulfonate molecules. The AM content was determined by a method involving a titration with HYAMINE™ titrant. The basic principles of the method are described in "Introduction to surfactant analysis", edited by D. C. Column, page 60, 1994. Further, AM content may be determined by the ASTM D6173 and ISO 2271 methods.

2. Free oil content (wt. % on 100% AM): content of non-ionic (organic) molecules, excluding the above-mentioned non-ionic N91-8 surfactant. Said free oil content was determined by a method involving High Pressure Liquid Chromatography (HPLC), thereby separating neutral compounds from the ionic compounds, and then correcting the obtained value for the amount of said N91-8. Further, free oil content may be determined by the ASTMD D3673 method.

3. NaOH content (wt. % on 100% AM): The NaOH content may be determined by titration with an acid (for example HCl).

4. $Na_2SO_4$ content (wt. % on 100% AM): The $Na_2SO_4$ content may be determined by the ASTM D6174 method.

EXAMPLES 1-10

In Examples 1-10, the experiments were performed as described above. In Table 2 below, further process parameters are shown. In Table 3 below, product components for the final product after hydrolysis are shown.

Examples 1 and 2 were performed under similar conditions, albeit slightly different amounts of caustic (NaOH) were used. Likewise, Examples 3 and 4 were performed under similar conditions, albeit slightly different amounts of caustic (NaOH) were used. Likewise, Examples 5 and 6 were performed under similar conditions, albeit slightly different amounts of caustic (NaOH) were used. Likewise, Examples 7 and 8 were performed under similar conditions, albeit slightly different amounts of caustic (NaOH) were used. Finally, Examples 9 and 10 were performed under similar conditions, albeit for Example 9 the molar $SO_3$/olefin ratio was 1.06 whereas that for Example 10 was 1.30.

TABLE 2

| | SULFONATION | | | | NEUTRALIZATION |
|---|---|---|---|---|---|
| | Temperature cooling water + feedstocks (° C.) | Type olefin feedstock | Olefin feed, kg/hour | $SO_3$/olefin[1], mole/mole | Type of reactor |
| Ex. 1 | 50 | I | 24.1 | 1.06 | loop |
| Ex. 2 | 50 | I | 24.1 | 1.06 | loop |
| Ex. 3 | 50 | I | 24.1 | 1.06 | loop |
| Ex. 4 | 50 | I | 24.1 | 1.06 | loop |
| Ex. 5 | 50 | I | 24.1 | 1.06 | WFE |
| Ex. 6 | 50 | I | 24.1 | 1.06 | WFE |
| Ex. 7 | 50 | I | 24.1 | 1.06 | WFE |
| Ex. 8 | 50 | I | 24.1 | 1.06 | WFE |
| Ex. 9 | 45 | II | 22.4 | 1.06 | WFE |
| Ex. 10 | 45 | II | 18.3 | 1.30 | WFE |

Ex. = Example; WFE = wiped film evaporator
[1]"$SO_3$/olefin" = $SO_3$ fed to sulfonation/olefin fed to sulfonation

| | NEUTRALIZATION (continued) | | HYDROLYSIS |
|---|---|---|---|
| | Residence time, minutes | AM, wt. %[1] | Residence time, minutes |
| Ex. 1 | 20 | 28.12 | 30 |
| Ex. 2 | 20 | 27.68 | 30 |
| Ex. 3 | 40 | 52.29 | 60 |
| Ex. 4 | 40 | 51.61 | 60 |
| Ex. 5 | 20 (*) | 26.59 | 30 |
| Ex. 6 | 20 (*) | 26.37 | 30 |
| Ex. 7 | 40 (*) | 55.36 | 60 |
| Ex. 8 | 40 (*) | 57.11 | 60 |
| Ex. 9 | 0 | n.d. | 60 |
| Ex. 10 | 0 | n.d. | 72 |

Ex. = Example; AM = active matter; n.d. = not determined
(*) Holding time between neutralization in the WFE and hydrolysis in the plug flow reactor
[1]Based on total amount of product from neutralization

TABLE 3

COMPONENTS FROM FINAL PRODUCT

|  | AM, wt. %[1] | Free oil[2], wt. % on 100% AM | NaOH, wt. % on 100% AM | Na$_2$SO$_4$, wt. % on 100% AM |
|---|---|---|---|---|
| Ex. 1 | 33.41 | 14.96 | 2.07 | 7.75 |
| Ex. 2 | 33.24 | 16.45 | 0.60 | 7.28 |
| Ex. 3 | 62.31 | 15.08 | 1.65 | 8.39 |
| Ex. 4 | 62.87 | 19.45 | 1.37 | 8.24 |
| Ex. 5 | 33.25 | 14.61 | 2.53 | 7.58 |
| Ex. 6 | 33.69 | 16.22 | 0.86 | 7.01 |
| Ex. 7 | 61.68 | 19.79 | 0.92 | 9.48 |
| Ex. 8 | 61.86 | 15.84 | 1.54 | 9.20 |
| Ex. 9 | 61.14 | 19.52 | 1.01 | 11.32 |
| Ex. 10 | 57.71 | 17.09 | 1.18 | 10.03 |

Ex. = Example; AM = active matter
[1]Based on total amount of product from hydrolysis
[2]Free oil content is exclusive of N91-8

In Table 4 below, product performance data are included in relation to a desired use of the internal olefin sulfonate products obtained in Examples 1-10, as a surfactant in chemical Enhanced Oil Recovery (cEOR). More in particular, so-called phase behaviour tests were conducted, as described below, in order to determine the "optimal salinity" and the "solubilisation parameter", the values for which are shown in Table 4.

Aqueous solutions comprising the surfactant composition and having different salinities were prepared. In tubes, the aqueous solutions were mixed with n-octane in a volume ratio of 1:1 and the system was allowed to equilibrate for days and weeks at 90° C. The alkane n-octane was used as a model oil for the screening tests, to represent a simple crude oil.

Microemulsion phase behaviour tests were carried out to screen surfactants for their potential to mobilize residual oil by means of lowering the interfacial tension (IFT) between the oil and water. Microemulsion phase behaviour was first described by Winsor in "Solvent properties of amphiphilic compounds", Butterworths, London, 1954. The following categories of emulsions were distinguished by Winsor: "type I" (oil-in-water emulsion), "type II" (water-in-oil emulsion) and "type III" (emulsions comprising a bicontinuous oil/water phase). A Winsor Type III emulsion is also known as an emulsion which comprises a so-called "middle phase" microemulsion. A microemulsion is characterised by having the lowest IFT between the oil and water for a given oil/water mixture.

For anionic surfactants, increasing the salinity (salt concentration) of an aqueous solution comprising the surfactant(s) causes a transition from a Winsor type I emulsion to a type III and then to a type II. Optimal salinity is defined as the salinity where equal amounts of oil and water are solubilised in the middle phase (type III) microemulsion. The oil solubilisation ratio is the ratio of oil volume ($V_o$) to neat surfactant volume ($V_s$) and the water solubilisation ratio is the ratio of water volume ($V_w$) to neat surfactant volume ($V_s$). The intersection of $V_o/V_s$ and $V_w/V_s$ as salinity is varied, defines (a) the optimal salinity and (b) the solubilisation parameter at the optimal salinity. It has been established by Huh that IFT is inversely proportional to the square of the solubilisation parameter (Huh, "Interfacial tensions and solubilizing ability of a microemulsion phase that coexists with oil and brine", J. Colloid and Interface Sci., September 1979, p. 408-426). A high solubilisation parameter, and consequently a low IFT, is advantageous for mobilising residual oil via surfactant EOR. That is to say, the higher the solubilisation parameter the more "active" the surfactant.

The detailed microemulsion phase test method used in these Examples has been described previously, by Barnes et al. under Section 2.1 "Glass pressure tube test" in "Development of Surfactants for Chemical Flooding at Difficult Reservoir Conditions", SPE 113313, 2008, p. 1-18, the disclosure of which article is incorporated herein by reference. In summary, this test provides two important data:

(a) the optimal salinity, expressed as % NaCl;
(b) the solubilisation parameter (SP, in ml/ml) at the optimal salinity (this usually takes several days or weeks to allow the phases to settle at equilibrium), wherein the interfacial tension (IFT, in mN/m) is calculated from the solubilisation parameter using the "Huh" equation IFT=0.3/SP2 as referred to above.

TABLE 4

|  | Optimal salinity, % NaCl | Solubilisation parameter |
|---|---|---|
| Ex. 1 | 0.9 +/− 0.2 | 30 |
| Ex. 2 | 0.9 +/− 0.2 | 30 |
| Ex. 3 | 0.5 +/− 0.2 | 35 |
| Ex. 4 | 0.5 +/− 0.1 | 30 |
| Ex. 5 | 1.1 +/− 0.2 | 40 |
| Ex. 6 | 1.1 +/− 0.3 | 45 |
| Ex. 7 | 0.6 +/− 0.2 | 45 |
| Ex. 8 | 0.6 +/− 0.2 | 45 |
| Ex. 9 | 0.9 +/− 0.2 | 50 |
| Ex. 10 | 2.0 +/− 0.2 | 45 |

Ex. = Example

The results in Examples 1-10 (see Table 3) show that internal olefin sulfonates can be prepared from internal olefins having an average carbon number that is equal to or greater than 20, by a process wherein said internal olefins are sulfonated using a cooling means (water) having a temperature which is greater than 35° C. (Examples 1-8: 50° C.; Examples 9-10: 45° C.), followed by contacting the thus sulfonated internal olefin with a base containing solution.

Still further, it appears from the results in Table 4 that the internal olefin sulfonates thus prepared can be advantageously used as a surfactant in chemical Enhanced Oil Recovery (cEOR) which requires them to lower the interfacial tension (IFT) between oil and water. This ability to lower the IFT is demonstrated by a relatively high solubilisation parameter for the internal olefin sulfonate products (see Table 4).

That which is claimed is:

1. A process for preparing an internal olefin sulfonate, comprising sulfonating an internal olefin, having an average carbon number that is equal to or greater than 20, in a sulfonation reactor into sulfonated internal olefin followed by contacting sulfonated internal olefin with a base containing solution, wherein the sulfonation reactor is cooled with a cooling means having a temperature which is greater than 35° C.

2. A process according to claim 1, wherein the average carbon number is from 20 to 40.

3. A process according to claim 1, wherein the temperature of the cooling means is from 40 to 60° C.

4. A process according to claim 1, wherein the cooling means is a cooling fluid.

5. A process according to claim 1, which is carried out continuously.

6. A process according to claim 1, wherein the base is a water soluble base and the solvent for the base is water.

7. A process according to claim 6, wherein the water soluble base is selected from the group consisting of hydroxides, carbonates and bicarbonates of an alkali metal ion, or of ammonium ion, and amine compounds.

8. A process according to claim 7, wherein the water soluble base is sodium hydroxide.

9. A process according to claim 1, wherein the temperature at which sulfonated internal olefin is contacted with the base containing solution is 0 to 250° C.

10. A process according to claim 1, wherein in the step wherein sulfonated internal olefin is contacted with the base containing solution, a non-ionic surfactant is added.

11. A process according to claim 10, wherein the non-ionic surfactant is an alkoxylate of an alcohol having an aliphatic group.

12. A process according to claim 1, wherein the step wherein sulfonated internal olefin is contacted with the base containing solution is carried out in a wiped film evaporator.

13. A process according to claim 4 wherein the cooling fluid is cooling water.

\* \* \* \* \*